(12) United States Patent
Goetz et al.

(10) Patent No.: US 6,985,088 B2
(45) Date of Patent: Jan. 10, 2006

(54) TELEMETRY MODULE WITH CONFIGURABLE DATA LAYER FOR USE WITH AN IMPLANTABLE MEDICAL DEVICE

(75) Inventors: Steven M. Goetz, Brooklyn Center, MN (US); Gregory Pat Spar, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 663 days.

(21) Appl. No.: 10/099,786

(22) Filed: Mar. 15, 2002

(65) Prior Publication Data

US 2003/0174066 A1 Sep. 18, 2003

(51) Int. Cl.
*H04Q 9/00* (2006.01)
(52) U.S. Cl. .................. 340/870.07; 607/5; 607/27; 607/30; 607/59; 607/60; 607/32; 600/523
(58) Field of Classification Search ........... 340/870.07; 607/5, 27, 30, 59, 60, 32; 600/523
See application file for complete search history.

(56) References Cited

U.S. PATENT DOCUMENTS

| | | | |
|---|---|---|---|
| 5,324,315 A * | 6/1994 | Grevious ..................... | 607/60 |
| 5,350,411 A * | 9/1994 | Ryan et al. .................. | 607/32 |
| 5,383,912 A | 1/1995 | Cox et al. | |
| 5,486,200 A * | 1/1996 | Lindemans ................... | 607/5 |
| 5,683,432 A | 11/1997 | Goedeke et al. | |
| 5,759,199 A * | 6/1998 | Snell et al. .................. | 607/60 |
| 5,833,623 A * | 11/1998 | Mann et al. ................. | 600/523 |
| 5,843,138 A | 12/1998 | Evers et al. | |
| 5,843,139 A | 12/1998 | Goedeke et al. | |
| 5,891,178 A * | 4/1999 | Mann et al. ................. | 607/27 |
| 5,938,690 A * | 8/1999 | Law et al. ................... | 607/46 |

* cited by examiner

*Primary Examiner*—Albert K. Wong
(74) *Attorney, Agent, or Firm*—Banner & Witcoff, Ltd.

(57) ABSTRACT

Disclosed is a method and apparatus for configuring an external device so that may communicate with and an implantable medical device in accordance with a desired telemetry protocols. The external device utilizes a telemetry module can be loaded with a protocol driver necessary for communicating with the implantable medical device. Once the desired protocol driver has been installed, the telemetry module and its associated external device, e.g., a physician programmer, are enabled to communicate with the implantable medical device.

11 Claims, 11 Drawing Sheets

TELEMETRY MODULE WITH CONFIGURABLE DATA LAYER FOR USE WITH AN IMPLANTABLE MEDICAL DEVICE

RELATED APPLICATION

This disclosure is related to the following co-pending application entitled "Telemetry Module With Configurable Physical Layer For Use With An Implantable Medical Device" by Goetz (U.S. patent application Ser. No. 10/099,785; filed Mar. 15, 2002), which is not admitted as prior art with respect to the present disclosure by its mention in this section.

FIELD OF THE INVENTION

The present invention generally relates to implantable medical devices. More particularly, the invention relates to configuration of a telemetry unit for transmitting data to and from an implantable medical device.

BACKGROUND OF THE INVENTION

The medical device industry produces a wide variety of electronic and mechanical devices suitable for use outside and inside the body for treating patient disease conditions. Devices used outside the body are termed external while devices used inside the body are termed implantable medical devices and include devices such as neurostimulators, drug delivery devices, pacemakers, defibrillators, and cochlear implants. Clinicians use implantable medical devices alone or in combination with therapeutic substance therapies and surgery to treat patient medical conditions. For some medical conditions, implantable medical devices provide the best, and sometimes the only, therapy to restore an individual to a more healthful condition and a fuller life.

Implantable medical devices can be used to treat any number of conditions such as pain, cancer, incontinence, movement disorders such as epilepsy, spasticity, and Parkinson's disease, and sleep apnea. Additionally, use of implantable medical devices appears promising to treat a variety of physiological, psychological, and emotional conditions.

Implantable medical devices have important advantages over other forms of therapeutic substance administration. For example, oral administration is often not workable because the systemic dose of the substance needed to achieve the therapeutic dose at the target sight may be too large for the patient to tolerate without very adverse side effects. Also, some substances simply will not be absorbed in the gut adequately for a therapeutic dose to reach the target sight. Moreover, substances that are not lipid soluble may not cross the blood-brain barrier adequately if needed in the brain. In addition, infusion of substances from outside the body requires a transcutaneous catheter, which results in other risks such as infection or catheter dislodgement. Further, implantable medical devices avoid the problem of patient noncompliance, namely the patient failing to take the prescribed drug or therapy as instructed.

For example, one type of medical device is an Implantable Neuro Stimulator (INS). The INS is implanted at a predetermined location in the patient's body. The INS generates and delivers electrical stimulation signals at neurostimulation sites or areas to influence desired neural tissue, tissue areas, nervous system and organs to treat the ailment of concern. The stimulation sites can also include the spinal cord, brain, body muscles, peripheral nerves or any other site selected by a physician. For example, in the case of pain, electrical impulses may be directed to cover the specific sites where the patient is feeling pain. Neurostimulation can give patients effective pain relief and can reduce or eliminate the need for repeat surgeries and the need for pain medications.

Implantable medical devices are often used in conjunction with various computer and telecommunication systems and components. Information obtained by the implantable medical device may be stored and subsequently transmitted to a physician or patient caregiver or a database on demand or automatically. Many ways of using the information are known including decision making to provide optimum medical care to the person with the medical condition.

For example, an external device such as a physician programmer can be used to allow a physician to communicate with the implanted medical device. The physician programmer allows the physician to create and store stimulation therapy programs for the patient to be delivered by the implanted medical device. The physician programmers also serve to recharge a rechargeable power source in the implanted medical device.

Typically, the physician programmer communicates bi-directionally with the implanted medical device via RF telemetry signals. The bi-directional communication between the medical device and the physician or patient programmer is typically accomplished via a telemetry module. The physician programmer, the patient programmer and the medical device each have respective telemetry modules that allow for bi-directional communication between the medical device and the programmers. The bi-directional telemetry communication, between the medical device and the physician or patient programmers is typically conduced at frequencies in a range from about 150 KHz to 200 KHz using existing telemetry protocols. A telemetry protocol is generally an agreed-upon format for transmitting data between two devices. The protocol can be implemented in hardware and/or software. The protocol determines, for example, the type of error checking to be used, the data compression method, if any, how the sending device will indicate that it has finished sending a message, how the receiving device will indicate that it has received a message, etc. There are a variety of protocols, each having particular advantages and disadvantages; for example, some are simpler than others, some are more reliable, and some are faster. Ultimately, the external device must support the right protocol(s) in order to communicate with implanted device.

Commercially available systems, however, are limiting in that the physician programmer is configured to provide telemetric communication using one or more pre-specified communication protocols. Accordingly, the physician programmer is typically only capable of communicating with those implanted medical devices that utilize those protocols. For each of the varying types of implanted devices available, the physician would need to have separate physician programmers that were compatible with each of the devices. Similarly, if the patient had more than one implanted device, the physician would likely need more than one physician programmer, one for each implanted device.

It is therefore desirable to provide a physician programmer that may be operated using any number of protocol schemes so that it may communicate with any number of implanted devices.

BRIEF SUMMARY OF THE INVENTION

In general, the present invention provides a method and apparatus for communicating via telemetry with an implanted medical device. A telemetry module is provided that can be configured with a protocol driver that allows communication with the implanted device. In a first embodiment of the present invention, an implantable medical device system is disclosed having a programming device, a telemetry module, and an implanted medical device. The physician programmer launches an application that requires some level of interaction with an implanted medical device and that is specific to the implanted medical device. Upon launching of the application, the physician programmer configures a data layer of the telemetry module to enable communication of the implanted device. In particular, the programmer installs an appropriate protocol driver within the telemetry module that is compatible with the implanted medical device. The telemetry module, once configured with the appropriate protocol driver, may then facilitate communication between the implanted device and the physician programmer. For example, at least initially, the implanted device can provide to the physician programmer various configuration parameters of the implanted device.

In other embodiments, the telemetry module may be physically resident within the physician programmer. Alternatively, the telemetry module may operate to interact with a patient programmer or any other general-purpose computing device such as a personal computer or a hand-held Personal Digital Assistant (PDA) device, thereby allowing any such device to communicate with the implanted medical device.

BRIEF DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

The present invention provides techniques for configuring a data layer of a telemetry module for communication with an implantable medical device. Although the present invention is described herein in conjunction with a neurostimulation system, those skilled in the art will appreciate that the present invention may be implemented to communicate within any number of implantable medical devices including, but not limited to, implantable drug delivery devices, pacemakers, defibrillators, and cochlear implants. In fact, one aspect of the present invention enables the external device to be a universal device that can communicate with any number of implanted devices.

Although not required, the invention will be described in the general context of computer-executable instructions, such as program modules. Generally, program modules include routines, programs, objects, scripts, components, data structures, etc. that perform particular tasks or implement particular abstract data types.

Figure 1:
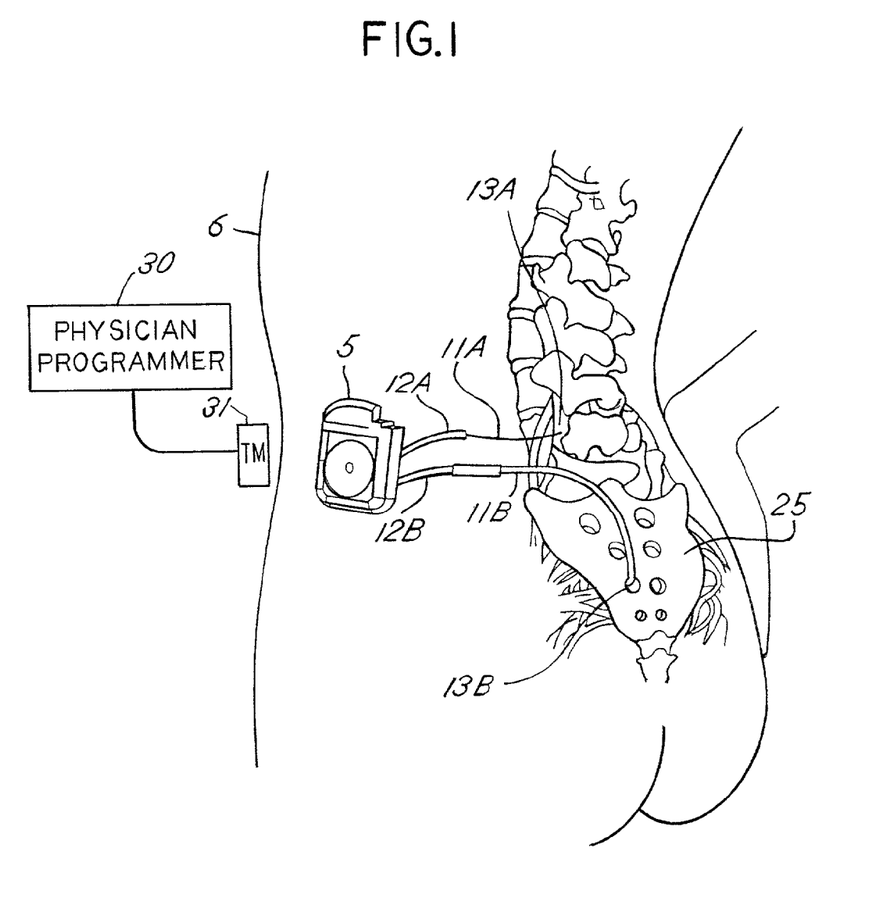
FIG. 1 is a schematic diagram of an exemplary implantable medical device system for use with the present invention.

Overview of an Implantable Medical Device System—FIG. 1 shows the general environment of an implantable medical device system in accordance with a preferred embodiment of the present invention. The implantable medical device system generally includes an implantable medical device 5, such as an Implantable Neuro Stimulator (INS), a lead 11A, a lead extension 12A, a physician programmer 30, and a telemetry module 31. The system also typically includes other components, such as a patient programmer, an external therapy delivery device, and optionally various sensors, which are not shown. U.S. patent application Ser. No. 10/002,328 entitled "Method and Apparatus for Programming an Implantable Device" filed on Nov. 1, 2001, which is incorporated herein by reference in its entirety, discloses one example of an implantable medical device system for use with the present invention.

Referring still to FIG. 1, the implantable medical device 5 is implanted in the body in a subcutaneous pocket at a site selected after considering physician and patient preferences, typically near the abdomen of the patient. In the case where the implantable medical device 5 is an INS, the device is a modified implantable pulse generator that will be available from Medtronic, Inc. with provisions for multiple pulses occurring either simultaneously or with one pulse shifted in time with respect to the other, and having independently varying amplitudes and pulse widths. The INS 5 contains a power source and other electronics to send precise, electrical pulses to the spinal cord, brain, or neural tissue to provide the desired treatment therapy.

The lead 11A is a small medical wire with special insulation. The lead 11A includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 11A may also be a paddle having a plurality of electrodes including, for example, a Medtronic paddle having model number 3587A. Alternatively, the lead 11A may provide electrical stimulation as well as drug infusion. Those skilled in the art will appreciate that any variety of leads may be used to practice the present invention depending upon the type of implantable medical device being used.

The lead 11A is implanted and positioned to provide treatment therapy to a specific site in the spinal cord or the brain. Alternatively, the lead 11A may be positioned along a peripheral nerve or adjacent neural tissue ganglia like the sympathetic chain or it may be positioned to provide treatment therapy to muscle tissue. In the case where electrical stimulation is to be provided, the lead 11A contains one or more electrodes (small electrical contacts) at a distal end 13A through which electrical stimulation is delivered from the implantable medical device 5 to the targeted neural tissue. If the spinal cord is to be stimulated, the lead 11A may have electrodes that are epidural, intrathecal or placed into the spinal cord itself. Effective spinal cord stimulation may be achieved by any of these lead placements.

The physician programmer 30, also known as a host programmer, uses a telemetry module (discussed further herein) to communicate with the implantable medical device 5, so a physician can program and manage a patient's therapy stored in the implantable medical device 5 and troubleshoot the implantable medical device system. An example of a physician programmer 30 is a Model 8840 Console Programmer soon to become available from Medtronic.

Figure 2:
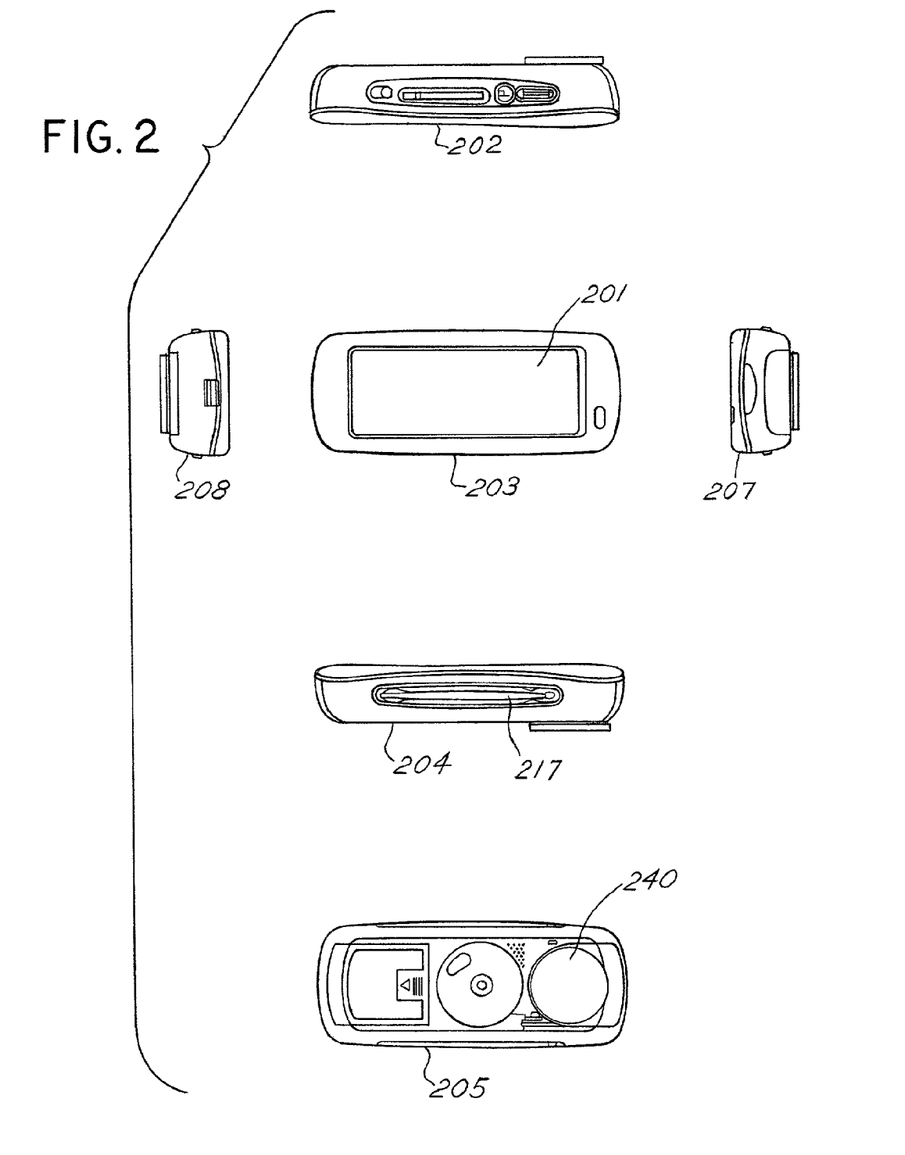
FIG. 2 depicts various views of a physician programmer in accordance with a preferred embodiment of the present invention.
Figure 3:
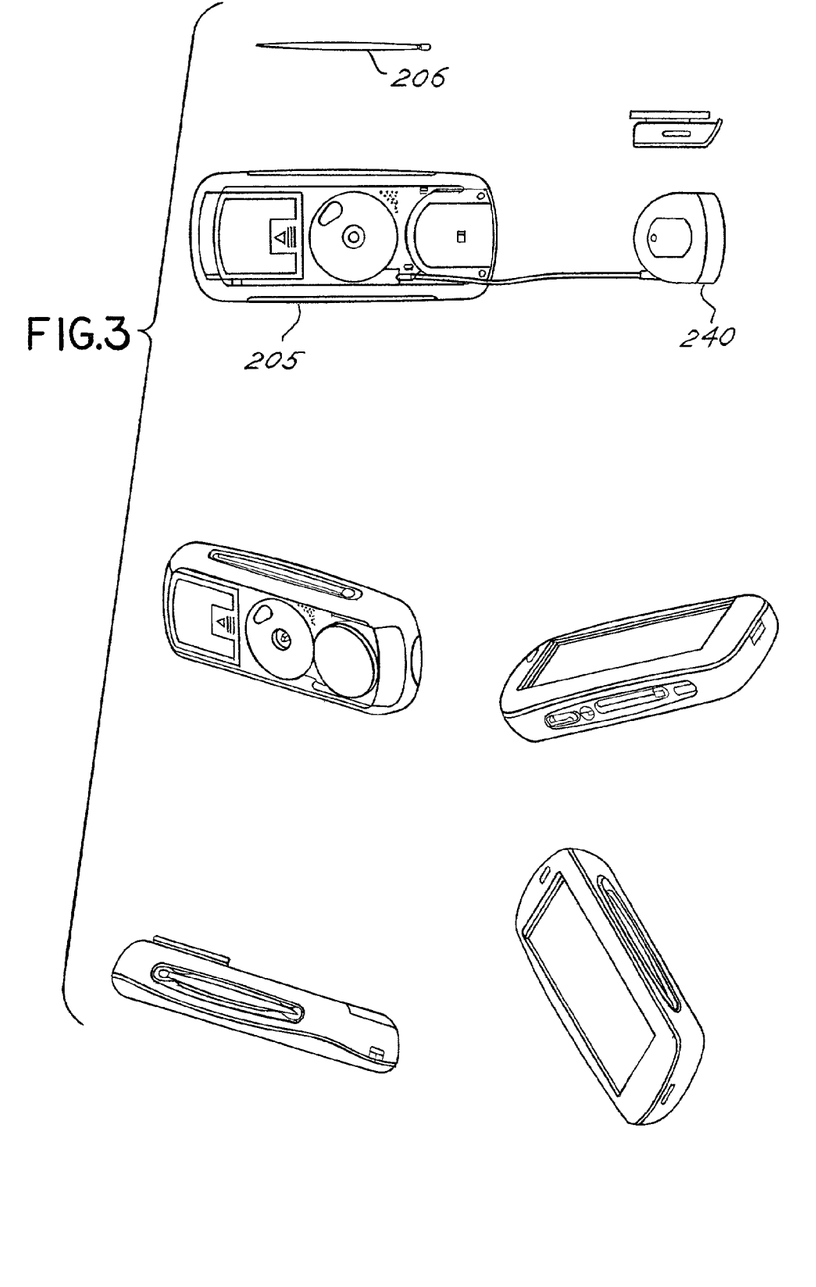
FIG. 3 depicts further various views of a physician programmer including the telemetry head in accordance with a preferred embodiment of the present invention.
Figure 4:
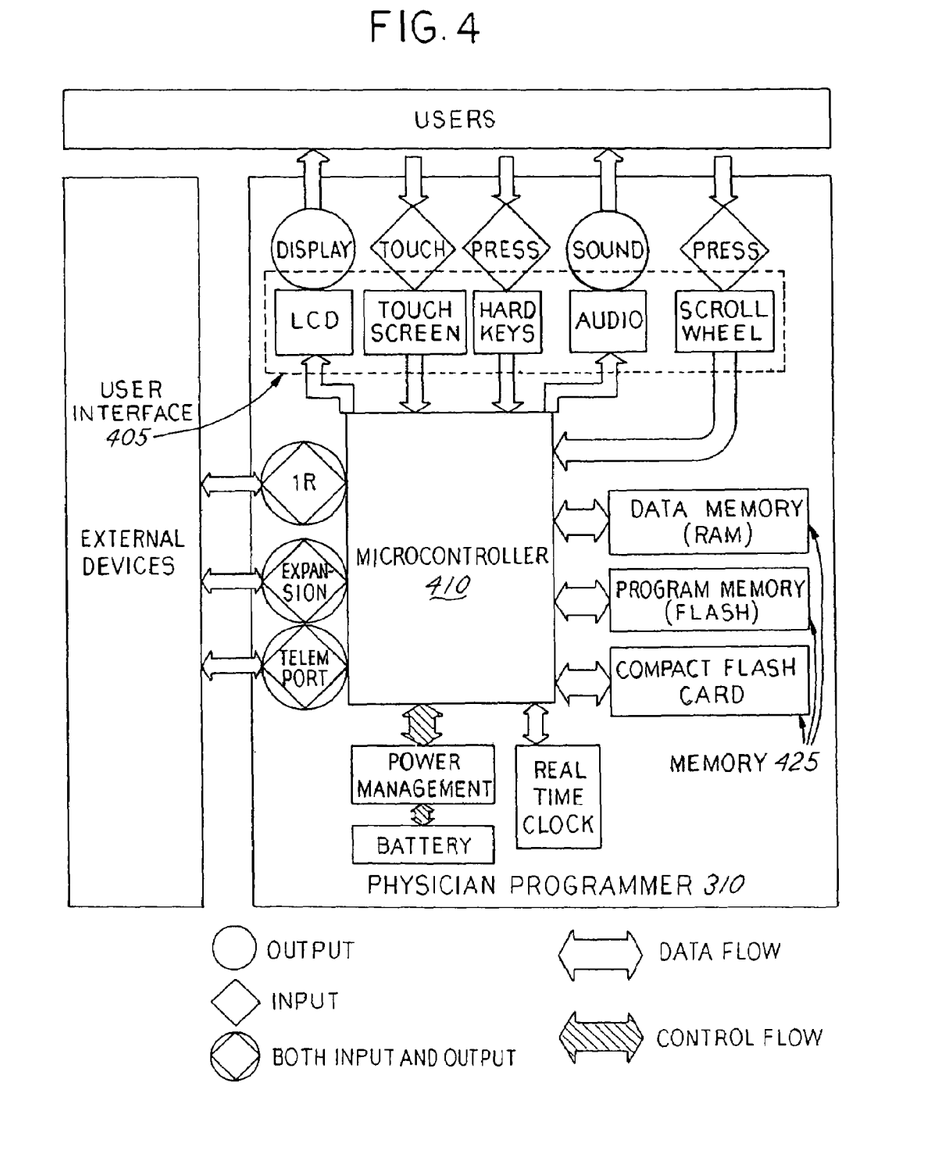
FIG. 4 is a schematic block diagram of an exemplary physician programmer for use with the present invention.

FIG. 2 depicts views of the physician programmer 30 including a front view 203, a top view 207, a bottom view 208, a back view 205, a left side view 202, and a right side view 204. The physician programmer 30 is preferably a portable computing device having a user interface. The user interface preferably includes a screen display 201 that is touch-sensitive to a pointing device 206 (FIG. 3), similar to that of Personal Digital Assistants (PDA) available today. On the dorsal side 217 of the physician programmer 30 is an area to receive and hold the telemetry module 240. FIG. 3 illustrates how the telemetry module 240 is insertable within a dorsal side 217 of the physician programmer 30. FIG. 4 depicts the general componentry of the physician programmer 30, which includes a user interface 405, a processor 410, a transmitter, and a receiver. The application program software for handling the functionality of the programmer 30 discussed herein may be stored in memory 425.

The physician programmer 30 acts as the control interface to the implanted medical device 5, which is generally dictated by the computer software application in the physician programmer. The software application generally has the following methods for implementing its control functionality: navigation methods; reporting methods; printing methods; data storage and transfer methods; data entry methods; methods to perform interrogation/review; methods to perform batch programming; user preferences; help methods; methods to resolve conflicts, and the like.

Figure 5:
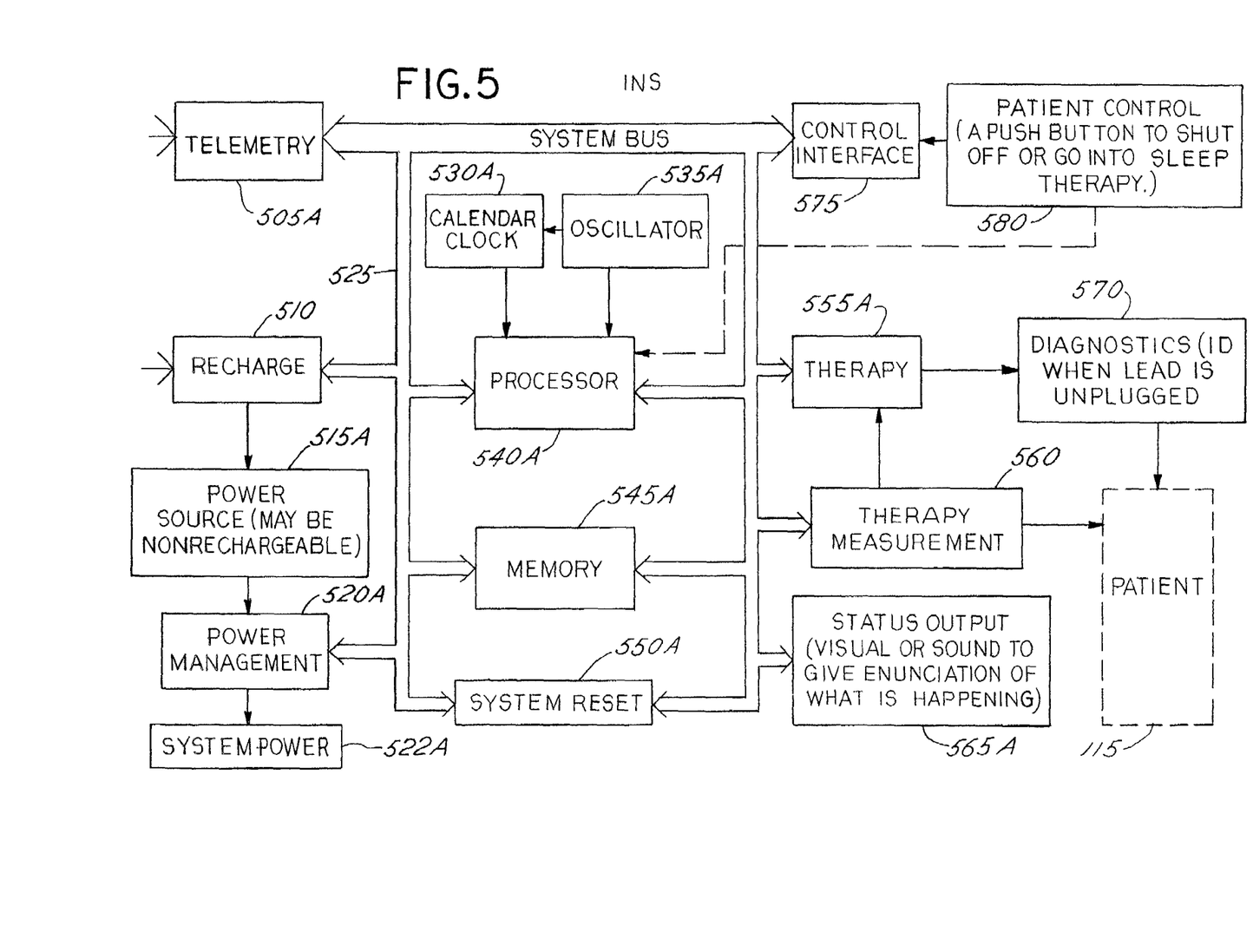
FIG. 5 is a schematic block diagram of an exemplary implantable neurostimulator for use with the present invention.

As expressed previously, the present invention may be implemented generally for use with any number of implantable medical device systems including, but not limited to, implantable drug delivery devices, pacemakers, defibrillators, and cochlear implants. In the embodiment where the implanted medical device is an INS, FIG. 5 provides a schematic block diagram of an exemplary INS 5. The INS generally includes a processor 540A with an oscillator 535A, a calendar clock 530A, memory 545A, and system reset 550A, a telemetry module 505A, a recharge module 510, a power source 515A, a power management module 520A, a therapy module 555A, and a therapy measurement module 560. Other components of the INS 5 can include, for example, a diagnostics module (not shown). All components except the power source 515A can be configured on one or more Application Specific Integrated Circuits (ASICs), may be part of one or more discrete components, or a combination of both. Also, all components except the oscillator 535A, the calendar clock 530A, and the power source 515A are connected to bi-directional data bus 525 that is non-multiplexed with separate address and data lines.

The processor 540A is synchronous and operates on low energy such as a Motorola 68HC11 synthesized core operating with a compatible instruction set. The oscillator 535A operates at a frequency compatible with the processor 540A, associated components, and energy constraints such as in the range from 100 KHz to 1.0 MHZ. The calendar clock 530A counts the number of seconds since a fixed date for date/time stamping of events and for therapy control such as circadian rhythm linked therapies. The memory 545A includes memory sufficient for operation of the INS 5 such as volatile Random Access Memory (RAM) for example Static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as the telemetry module 505A, so the telemetry module 505A can request control of the data bus 525 and write data directly to memory 545A bypassing the processor 540A. The system reset 550A controls operation of ASICs and modules during power-up of the INS 5, so ASICs and modules registers can be loaded and brought on-line in a stable condition.

All component of the INS 5 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones. Those skilled in the art will appreciate that the INS 5 may be configured in a variety of versions by removing modules not necessary for the particular configuration and by adding additional components or modules.

Overview of the Telemetry Module—Referring back to FIG. 3, the telemetry module 240 is a relatively small device used to conveniently provide communication between the physician programmer 30 and the implanted medical device 5. The telemetry module 240 includes a programming head designed to support multiple existing and future implantable medical devices. The telemetry module 240 communicates directly with the implanted medical device via a modulated inductive link and with a host programming instrument (e.g., a physician programmer), preferably by means of a cable, but may be any sort of connection including, for example without limitation, RF and infrared.

Although in the preferred embodiment discussed herein the telemetry module 240 interacts with the physician programmer 30 as a separate device, those skilled in the art will appreciate that other embodiments are conceivable and still considered within the scope of the present invention. For example, the telemetry module 240 may be physically resident within the physician programmer 30 or any other programming device for use with an implantable medical device. Alternatively, the telemetry module 240 may operate to interact with a patient programmer or any other general-purpose computing device such as a personal computer or a hand-held Personal Digital Assistant (PDA) device, thereby allowing any such device to communicate with the implanted medical device 5.

Figure 6:
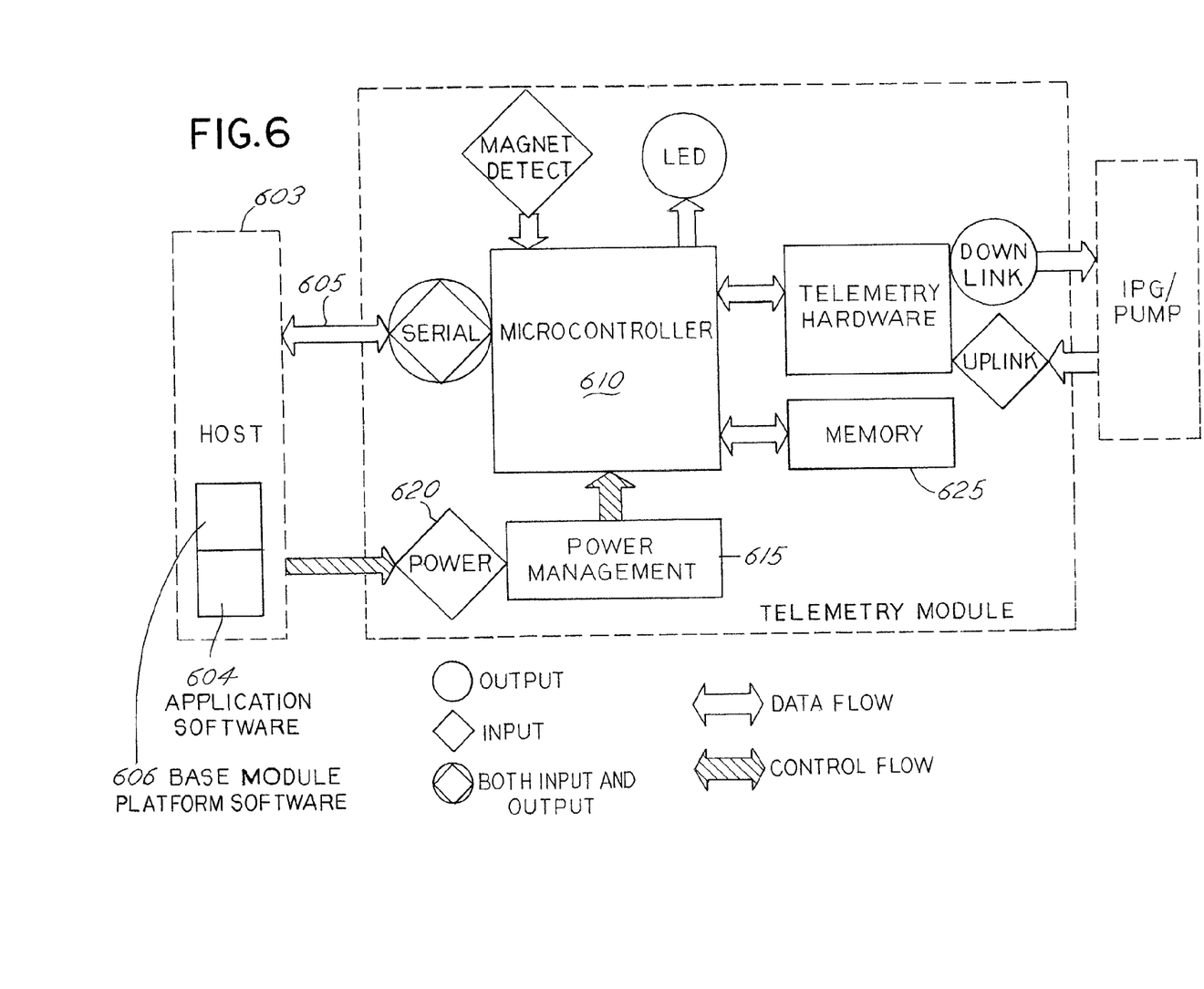
FIG. 6 is a schematic block diagram of a telemetry module in accordance with a preferred embodiment of the present invention.

FIG. 6 is a schematic block diagram depicting the various components of the telemetry module 240 in accordance with a preferred embodiment of the present invention. The telemetry module 240 generally includes a host interface 605 (e.g., an interface to a physician programmer), a microcontroller 610, a power management module 615, a source of power 620, telemetry hardware, memory, and uplink and downlink interfaces to the implanted medical device. In this embodiment, the telemetry module 240 is a microprocessor-based device that includes software to control its functionality. Those skilled in the art will appreciate that the present invention may also be implemented using discrete logic-based or other circuitry.

The host interface 605 is preferably an asynchronous, full duplex serial port. The host interface 605, attaches directly to the telemetry module head itself and provides both power and a serial interface for messages and commands to and from the host 603. The source of power 620 is preferably provided by the host 603 having a voltage range of 4.0 and 12.0 volts, with 8.8 volts for optimal telemetry downlink power and 3.3 volts for use by the digital sections of the telemetry module 240. Those skilled in the art will appreciate that the telemetry module 240 may be powered in any number of ways including power supplied by the host and/or an internal power source (e.g., one or more batteries) in the telemetry module 240 itself. A regulator (not shown) supplies power to the analog receiver portions of telemetry module 240.

The memory 625 preferably includes FLASH memory as well as RAM memory. The FLASH memory may store platform firmware as well as up to nine protocol drivers (discussed herein). Of course, with more memory or with smaller drivers, the number of stored protocol drivers could be arbitrarily larger (or smaller). One or more 64K byte sectors may be used for protocol driver execution or to store factory information, such as device serial number. The FLASH is connected to allow in-circuit programming, allowing both the platform code for the telemetry module 240, or individual protocol drivers to be saved or upgraded in its memory. An internal 4K RAM space is provided primarily for storage of STACK and possibly some critical global variables. An external SRAM may also be provided, which shares an address and data bus with the FLASH memory.

Figure 7:
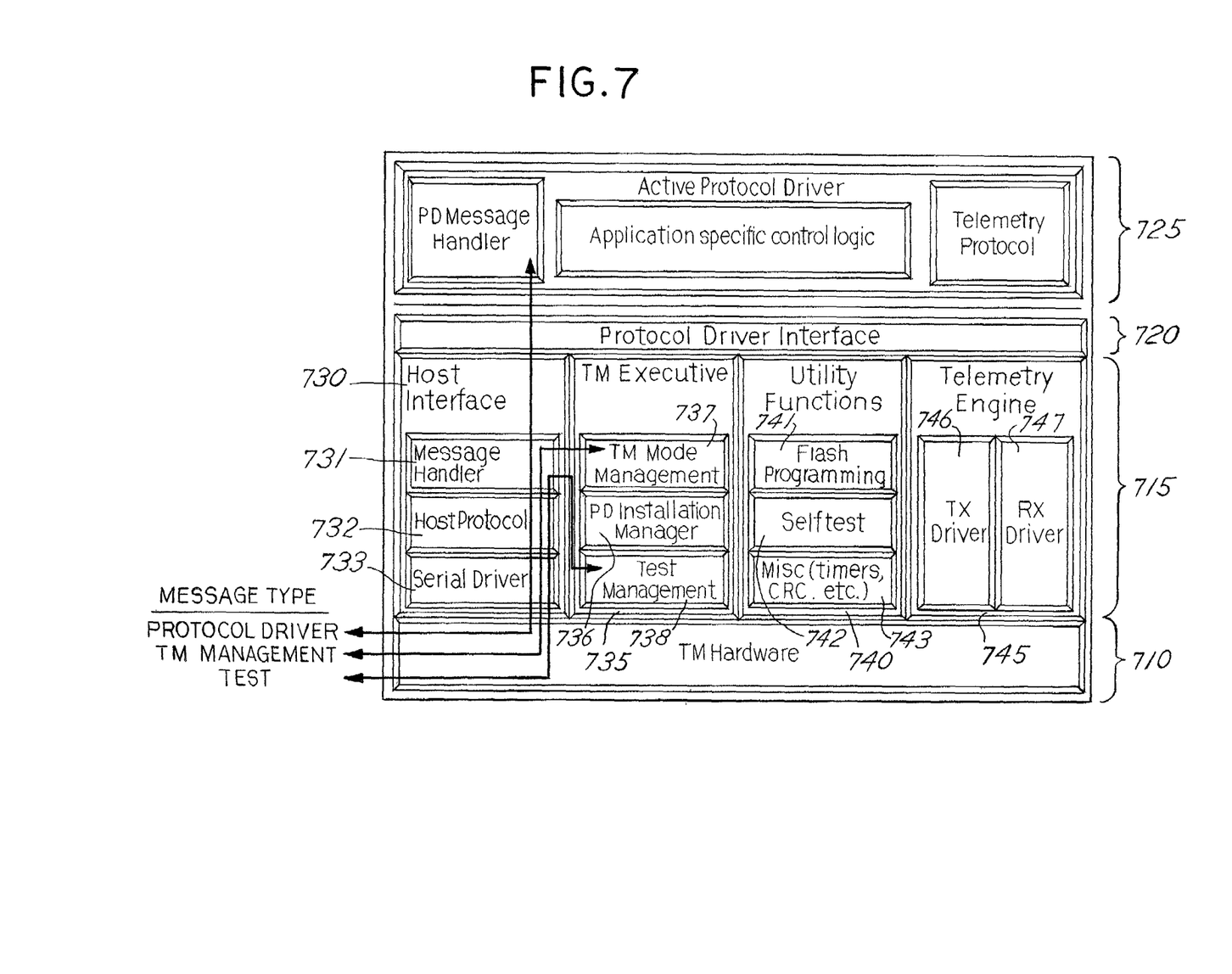
FIG. 7 is a schematic block diagram depicting the various software and hardware components of a telemetry module in accordance with a preferred embodiment of the present invention.

FIG. 7 is a schematic block diagram of the hardware and software components of the telemetry module 240 in accordance with a preferred embodiment of the present invention. Resident within memory 625 is software, which is subdivided into functions that are common across all uses of the telemetry module 240 (called the platform software 715) and functions that are specific to a particular protocol (called a protocol driver 725). The platform aspect of the telemetry module software is permanently resident within the telemetry module hardware itself. These components (platform software 715, the platform hardware 710, and the protocol driver interface 720) comprise the telemetry module platform that then host one or more installable protocol drivers 725. The protocol driver 725 is generally a program that acts as a translator between the implanted device and application programs 604 that use the device. Each implanted device has its own set of specialized commands that only its driver knows. In contrast, most programs access devices by using generic commands. The protocol driver 725, therefore, accepts generic commands from a program and then translates them into specialized commands that are understood by the implanted device.

The platform software 715 controls the basic features of the platform hardware 710 and interfaces with the host 603 and the telemetry transceiver. For example, the platform software 715 handles initial boot procedure and initializations, manages the operational modes of the telemetry module 240, and manages the installation and subsequent launching of the protocol driver software. To support the operation of protocol driver software, the platform software 715 operates with the protocol driver interface 720, which provides a standardized interface that abstracts and encapsulates all of the functionality necessary for the protocol driver operations.

The platform software 715 functions are implemented across several distinct subsystems including, but not limited to, a host interface 730, a telemetry module executive 735, a block of utility functions 740, and a telemetry engine 745. The host interface 730 manages the serial channel communications with the host programming instrument. The host interface 730 includes a serial driver 733, a host protocol 732, and a message handler 731. The message handler 731 serves to process the various messages that can be received over the host interface 730 and routes them appropriately. In particular, the message handler 731 manages the serial driver 733, identifies the intended source and the validity of received messages, routes messages not intended for the basic telemetry module platform (e.g., test and protocol driver messages), responds appropriately to all other messages with either an acknowledgement of proper reception and routing, or with the expected data, and intercepts and acts on special message commands to facilitate non-standard features that exist outside the normal message protocol (e.g., reset command, override commands, etc.).

The telemetry module executive 735 handles basic operational modes of the telemetry module 240 and some of the built-in functions of the telemetry module 240 including, for example, the installation procedures for protocol driver 725, protocol driver verification and launching procedures, and test mode management facilities. For these exemplary functions, the telemetry module executive 735 includes a protocol driver installation manager 736, a telemetry module mode management module 737, and a test management module 738, respectively. The block of utility functions 740 include a self-test operations module 741, flash erasing and writing tools (in flash programming module 742), general purpose algorithms 743 (e.g., Cyclic Redundancy Check (CRC), checksum, etc.), and provisions for the other resources that are provided to the protocol driver 725 (e.g., timers, revision and ID information, etc.). The telemetry engine 745 holds a transmit driver 746 and a receive driver 747 and other primitive operations for the generation of and reception of telemetry waveforms.

Figure 8:
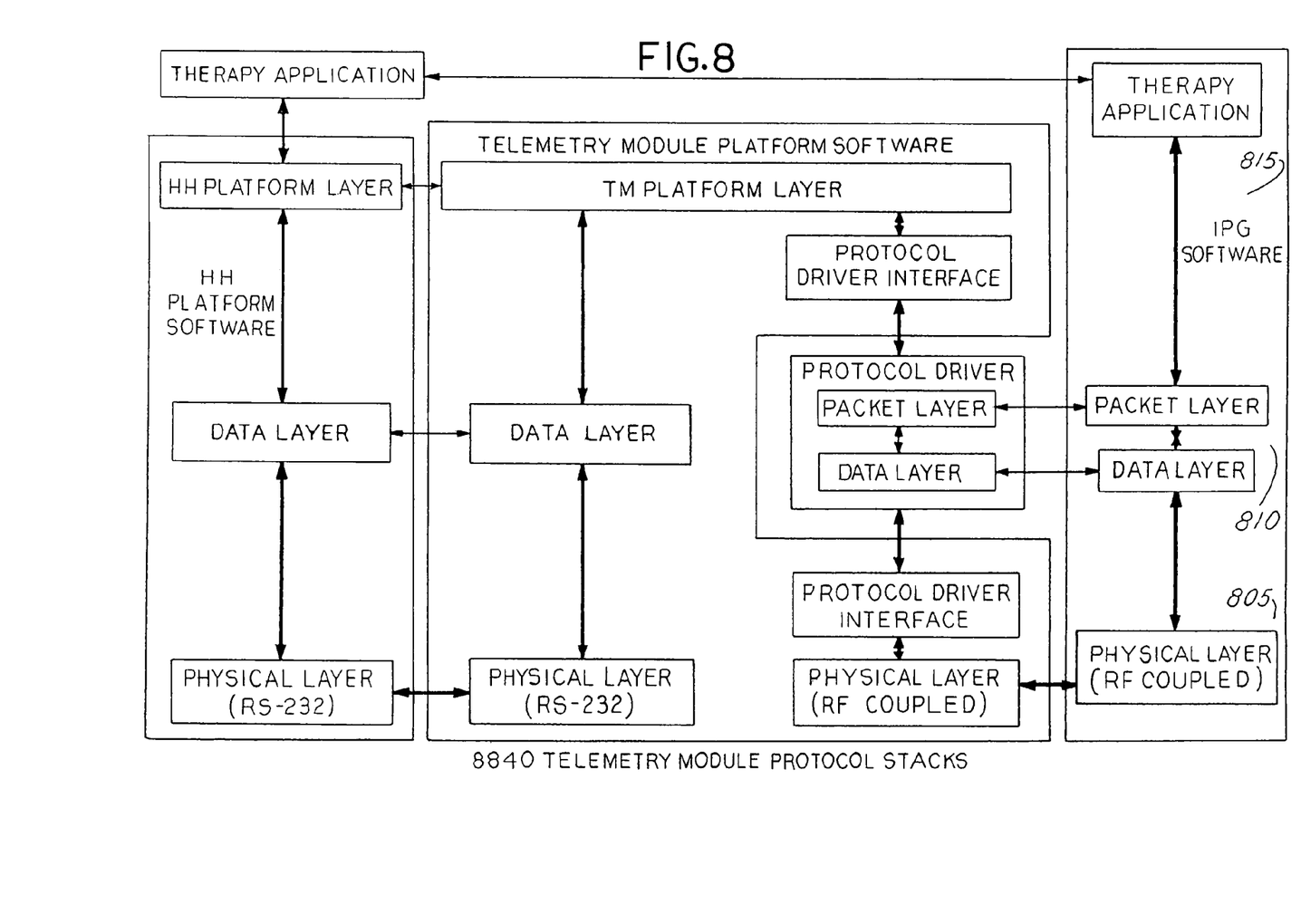
FIG. 8 is a schematic block diagram depicting the software layers for handling communications between a physician programmer, a telemetry module, and an implantable medical device in accordance with a preferred embodiment of the present invention.

The overall system includes a three-layer protocol stack that adds robustness to the serial channel physical layer. FIG. 8 provides an illustration of the protocol layers of the telemetry module 240. Above the physical layer 805 are a data layer 810 and ten a platform layer 815. The platform layer 815 is where messages are firmed and sent, and where responses are received and processed. The data layer 810 is where the physical integrity (framing, CRC checking etc.) of all received information is accomplished. Platform Layer Messages (PLM) are passed to the data layer 810, which manages the actual transmission of the message. To accomplish this the data layer 810 adds two items to the PLM; a header containing frame type and size information, and a CRC trailer used for validation. The completed product is called a "frame." There are three frame types. Messages to or from the Platform layer are frame type "DATA". The "ACK" and "NAK" frame types are assigned to messages that originate within the Data Layer, and are used to validate transmission of "DATA" frames. A completed FRAME is buffered in the data layer 810 (in case of the need for re-transmission), and then sent through the physical Layer 805 for actual transmission. One example for configuring the physical layer is disclosed in copending application entitled "Telemetry Module With Configurable Physical Layer For Use With An Implantable Medical Device" by Goetz (U.S. patent application Ser. No. 10/099,385; filed Mar. 15, 2002) which is incorporated herein by reference. As discussed herein and in accordance with a preferred embodiment of the present invention, the data layer 810 may be configured by the application software with an appropriate protocol driver to operate in accordance with a desired telemetry protocol.

Those skilled in the art will appreciate that the telemetry module 240 may contain other hardware/software structures and still be able to incorporate the features of the present invention. In addition, those skilled in the art will appreciate that there may be any number of varying connections to the host 603 (e.g., from a cable to some form of wireless connection).

Figure 9:
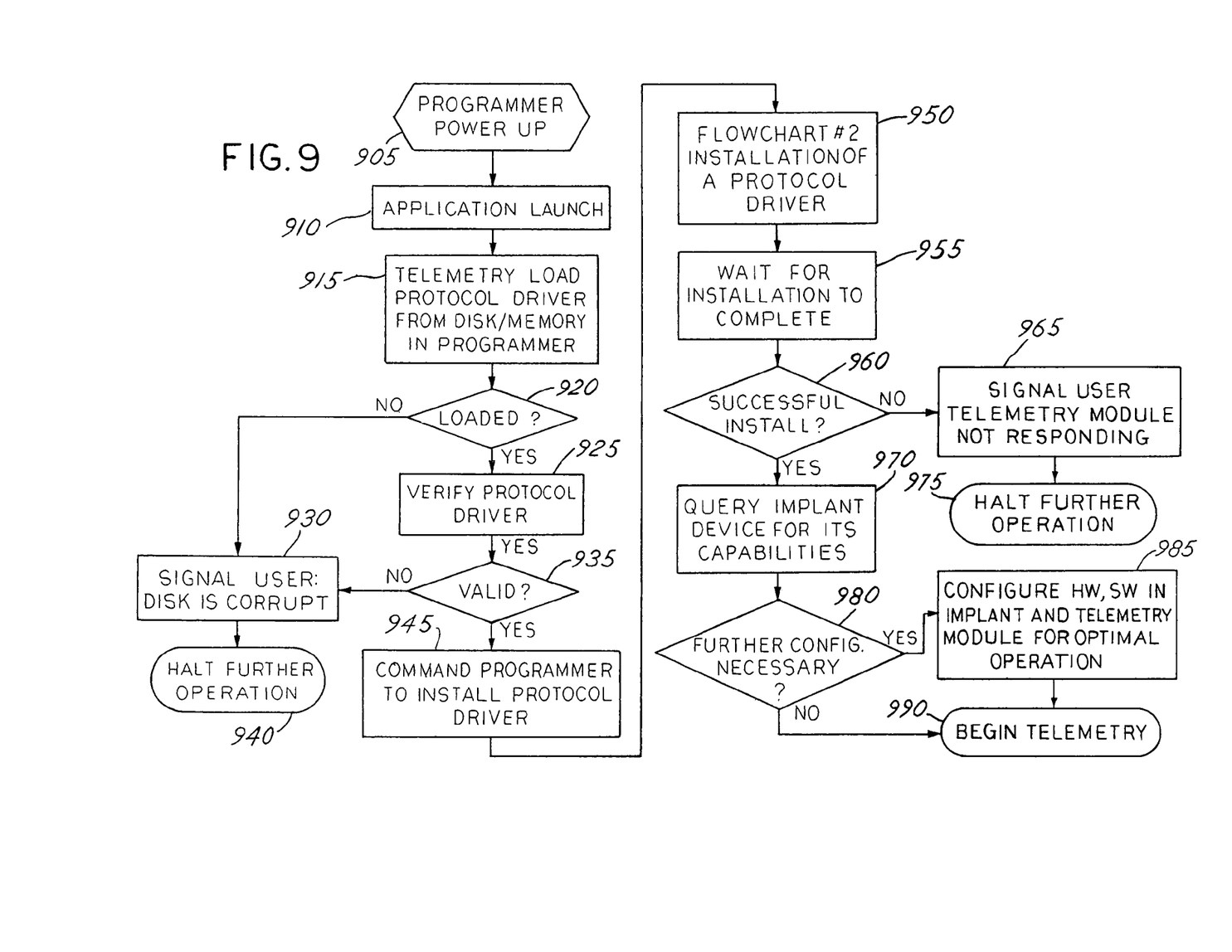
FIGS. 9–10 are flow charts illustrating the processes for configuring a telemetry module to enable communications with an implantable medical device in accordance with a preferred embodiment of the present invention.

FIG. 9 illustrates a flow chart illustrating the process for configuring a telemetry module 240 by the application software 604. The host 603 (e.g., physician programmer) includes a base module platform software 606 that manages the various procedures for configuring the telemetry module 240. The base module platform software 606 generally includes mechanisms for identifying the desired protocol driver 725 from among several saved on a card or in memory, checking the integrity of the protocol driver 725, communicating with the telemetry module 240 to initiate the transfer, transferring the binary data that comprises the protocol driver 725, and verifying the integrity of the transfer. The telemetry module 240 includes an operating system that performs secondary operations for protocol installation, including, for example, loading the protocol driver 725 into memory.

Referring still to FIG. 9, at step 905, the host device 603 (e.g., physician programmer) is turned on and, at step 910, the host 603 launches in response to user input an application program 604. The application program 604 and corresponding protocol driver 725 may be stored in a memory such as compact flash card. The application program 604 preferably includes, as part of its file structure, a file containing the protocol driver 725 that it uses for its telemetric communications. As part of its startup activities, the application program 604 points the base module platform software 606 to this file. The application program 604 then instructs the base module platform software 606 to have the protocol driver 725 installed.

At step 915, the base module platform software 606 opens the protocol driver file and loads it into memory. At step 920, the host 603 confirms whether the protocol driver 725 is loaded. If it has not loaded, at step 930, the host 603 signals the user that the driver has not loaded (typically, due to a corrupt flash card) and, at step 940, halts further operation. If the protocol driver 725 has loaded, at step 925, the host 603 verifies that the protocol driver 725 is a valid. If loading of the protocol driver 725 is not valid, at step 930, the host 603 signals the user that the driver has not loaded and, at step 940, halts further operation. If the loading of the protocol driver 725 is valid, at step 945, the host 603 installs the protocol driver 725 in the telemetry module 240.

At step 950, the protocol driver 725 is installed in the telemetry module 240. This procedure is described in further detail herein. At step 955, the installation process continues until it is complete and, at step 960, the host 603 may perform certain checks to determine whether the installation was successful. If the installation was successful, the telemetry module 240 is ready to initiate communication and, at step 970, queries the implanted device for its communications capabilities and, at step 980, determines whether the telemetry module 240 requires further configuration. If no further configuration is necessary, which is likely to be the case for most existing implanted devices, the telemetry module 240 is ready to begin telemetric communication, at step 990. If further configuration is necessary, at step 985, the telemetry module 240 configures the hardware and software in the implanted device and the telemetry module 240 for optimal operation. Configuration parameters may include, for example, data rate, telemetry scheme, etc. As discussed, one example for configuring the physical layer of the telemetry module 240 is disclosed in co-pending application entitled "Telemetry Module With Configurable Physical Layer For Use With An Implantable Medical Device" by Goetz (U.S. patent application Ser. No.10/099,385; filed Mar. 15, 2002)

Figure 10:
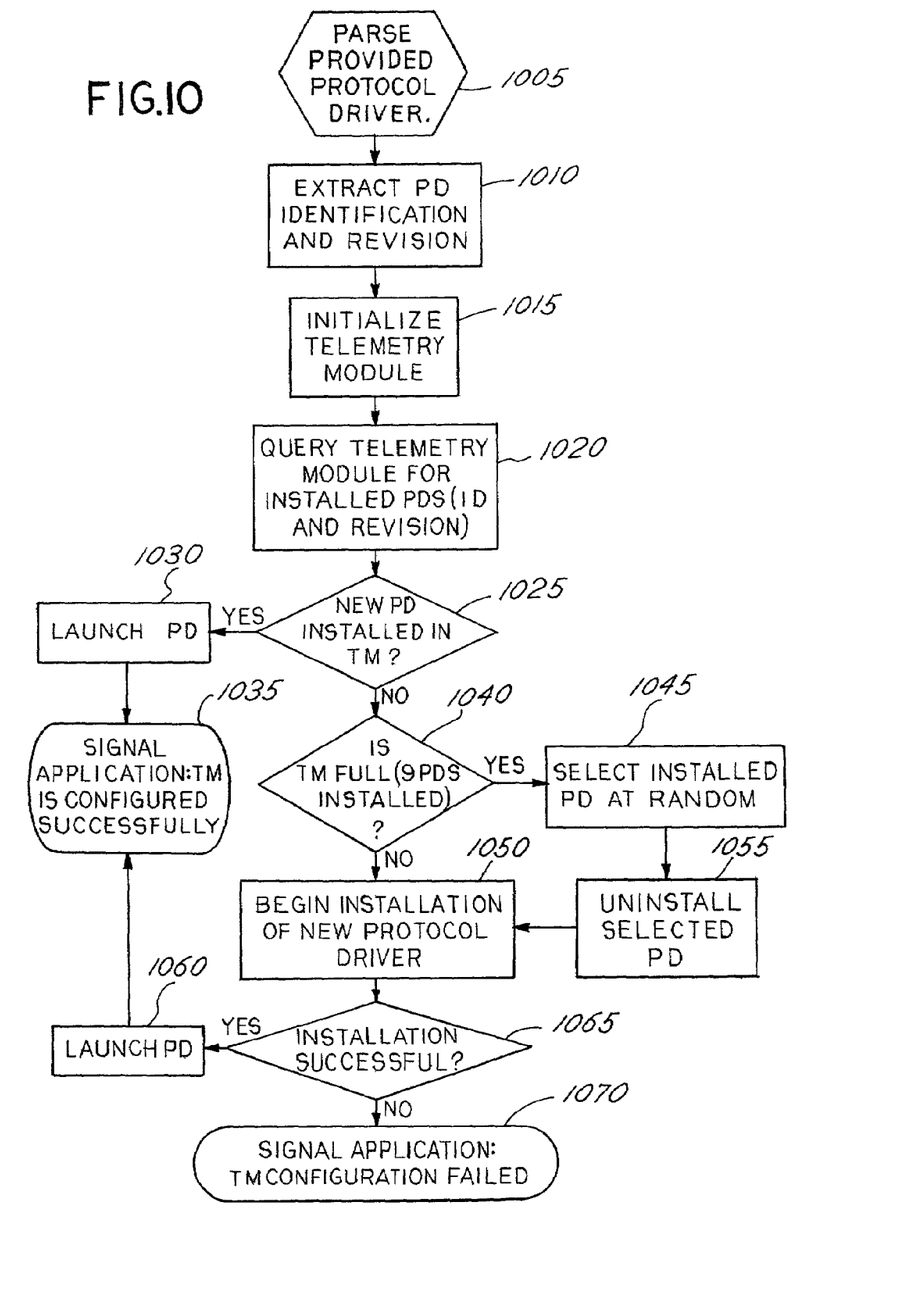

FIG. 10 is a flow chart providing a more detailed description of the installation of the protocol driver 725 procedure, including steps 950 and subsequent steps. At step 1005, the base platform module of the host 603 parses the protocol driver 725 and, at step 1010, extracts the identification number and revision number of the protocol driver 725. Each protocol driver 725 preferably has a unique identification number and a revision number to provide information regarding any possible updates to the protocol driver 725. At step 1015, the host 603 initializes the telemetry module 240 to ensure that it is operating properly. At step 1020, the host 603 queries the telemetry module 240 for installed protocol drivers 725, particularly the identification number and revision number of each installed protocol driver 725. At step 1025, the host 603 checks whether the protocol driver 725 to be installed is already installed in the telemetry module 240. If it is, then there is no need to reinstall the protocol driver 725 and, at step 1030, the telemetry module 240 is instructed to launch the desired protocol driver 725. At step 1035, the telemetry module 240 signals the application 604 in the host 603 that the telemetry module 240 is successfully configured for communication with the implanted device and, at step 1060, launches the protocol driver 725.

If the desired protocol driver 725 is not already installed, then further processing is necessary to proceed with the installation. At step 1040, the telemetry module memory is checked to see if it is full. For example, the telemetry module 240 may be capable of storing a maximum of nine protocol drivers 725. If the telemetry module memory is not full, at step 1050, the host 603, in concert with the telemetry module operating system, installs the desired protocol driver 725 into the telemetry module 240. If the telemetry module memory is full, at step 1045, the host 603 randomly selects protocol driver 725 in the telemetry module memory, and at step 1055, uninstalls the randomly selected protocol driver 725. At step 1050, the host 603, in concert with the telemetry module operating system, installs the desired protocol driver 725 into the telemetry module 240.

At step 1065, the telemetry module 240 confirms whether the installation was successful. If yes, at step 1060, the telemetry module 240 launches the protocol driver 725. If no, the telemetry module 240 signals the host 603 that the telemetry module configuration failed.

Advantageously, the telemetry module 240 may be upgraded, for example by installing hardware or software to enable faster telemetry, without requiring replacement of the physician programmer.

Figure 11:
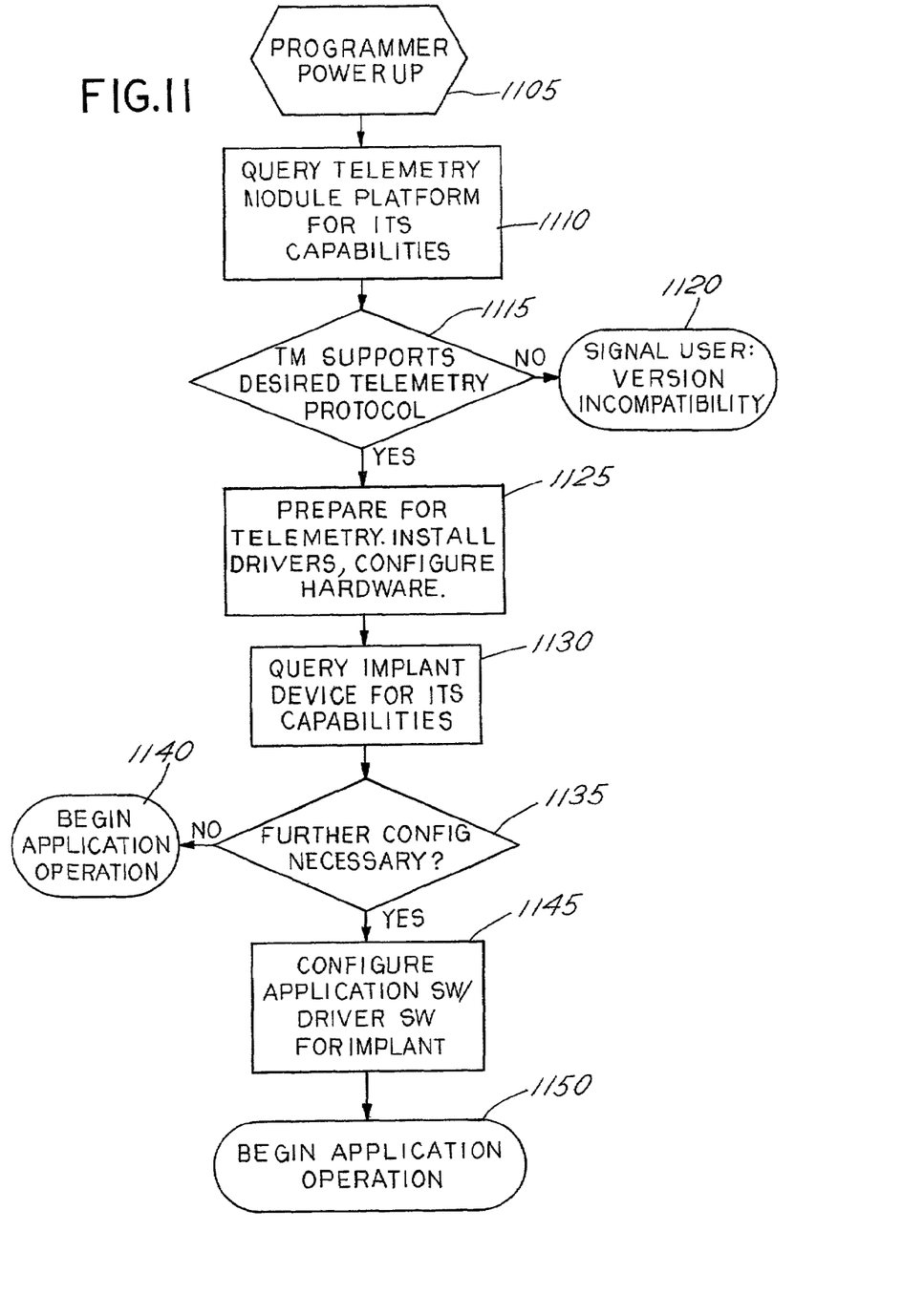
FIG. 11 is another flow chart illustrating the processes for configuring a telemetry module to enable communications with an implantable medical device in accordance with another preferred embodiment of the present invention.

In accordance with another embodiment of the present invention, the telemetry head may be dynamically configured to simultaneously support various configurations of any chosen telemetry protocol. For example, a telemetry protocol may be further configured to enable optimal communication efficiency and data integrity. For example, U.S. patent application Ser. No. 09/665,874, entitled "Telemetry Modulation Protocol System For Medical Devices" and filed on Sep. 20, 2000, which is incorporated herein by reference in its entirety, discloses one such telemetry scheme that can be further configured. FIG. 11 is a flow chart illustrating the process for dynamically configuring a telemetry module 240. At step 1105, the host 603 is turned on, which launches an application program 604 corresponding to the implanted medical device. At step 1110, the host 603 queries the telemetry module platform for its capabilities. For examples, the telemetry module platform may provide information such as its parameter, parameter ranges, parameter resolutions, etc. At step 1115, the host 603 checks whether the telemetry module 240 can support the desired protocol. If no, at step 1120, the host 603 signals the user that the telemetry module 240 is incapable of supporting the desired telemetry protocol. If yes, at steps 1125 through 1150, the telemetry module 240 is prepared for telemetry communication in accordance with the procedures described above.

Although described for use with a physician programmer, the telemetry module 240 of the present invention may also be implemented for use with host devices other than the physician programmer including, but not limited to, a general purpose computing device such as a personal computer, a laptop or a hand-held device, or a cellular device.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

What is claimed is:

1. A method for configuring an external telemetry unit to enable communication between an external device and an implantable medical device comprising the steps of:
   (a) identifying at least one appropriate telemetry protocol for use with the implantable medical device;
   (b) loading from memory a protocol driver associated with one of the identified telemetry protocols;
   (c) installing the protocol driver within the external telemetry unit; and
   (d) initiating telemetric communication between the external telemetry unit and the implantable medical device in accordance with the identified telemetry protocol.

2. The method of claim 1, wherein the step of installing the protocol driver includes the steps of: (i) identifying from the telemetry module already installed protocol drivers; and (ii) comparing the protocol driver with the already installed protocol drivers to determine whether the protocol driver has already been installed.

3. The method of claim 2, wherein the step of installing the protocol driver further includes the step of: (iii) determining whether the telemetry module can install another protocol driver.

4. The method of claim 3, wherein the step of installing the protocol driver further includes the step of: (iv) if the telemetry module can install another protocol driver, installing the protocol driver; and (v) if the telemetry module cannot install another protocol driver, uninstalling an already installed protocol driver and then installing the protocol driver.

5. A computer-readable medium having computer-executable instructions for performing the steps recited in claim 1.

6. A system for communicating with an implantable medical device comprising in combination:
   (a) an external telemetry unit for providing telemetric communication with an implanted device; and
   (b) a host device in communication with the external telemetry unit having stored herein an application for use with the implanted medical device and a base module platform software for configuring the telemetry unit with a protocol driver to operate with an appropriate telemetry protocol.

7. The system of claim 6, wherein the host device is a physician programmer.

8. The system of claim 6, wherein the host device is a patient programmer.

9. The system of claim 6, wherein the host device is a general-purpose computing device.

10. The system of claim 9, wherein the general-purpose computing device is selected from the group consisting of a personal computer, a laptop computer, and a hand-held device.

11. A configurable telemetry unit for communicating with an implantable medical device comprising in combination:
   (a) a host interface for receiving a protocol driver to enable communication with the implantable medical device in accordance with a telemetry protocol recognized by the implantable medical device;
   (b) an operating system for performing secondary operations for installing the protocol driver;
   (c) an antenna for transferring signals to and from the implantable medical device via telemetry; and
   (d) a protocol driver interface for receiving a signal from the protocol driver, generating a transmit signal having parameters specified by the protocol driver, and providing the transmit signal to the antenna.

* * * * *